United States Patent [19]
Dejardin et al.

[11] Patent Number: 5,236,592
[45] Date of Patent: Aug. 17, 1993

[54] HAEMOCOMPATIBLE COMPOSITE MATERIAL AND METHOD OF USING THEREOF

[75] Inventors: Philippe Dejardin; Feng Yan, both of Strasbourg; Adrien Schmitt, Mundolsheim, all of France

[73] Assignee: Hospal Industrie, Meyzieu, France

[21] Appl. No.: 719,245

[22] Filed: Jun. 21, 1991

[30] Foreign Application Priority Data

Jun. 25, 1990 [FR] France ................ 90 07984

[51] Int. Cl.⁵ .............................. B01D 61/00
[52] U.S. Cl. ...................... 210/646; 210/500.35; 210/500.43; 424/487; 523/112
[58] Field of Search ............ 210/500.35, 500.43, 210/638, 490, 654, 646; 427/245, 246; 424/78, 79, 486, 487, 78.08, 78.31, 78.35; 523/112

[56] References Cited

U.S. PATENT DOCUMENTS

| | | | |
|---|---|---|---|
| Re. 27,401 | 6/1972 | Wichterle | 210/500.35 |
| 3,616,930 | 2/1971 | Muir | 210/500.43 |
| 3,799,355 | 3/1974 | Salyer et al. | 210/500.43 |
| 3,839,200 | 10/1974 | Gigou et al. | 210/500.43 |
| 4,025,439 | 5/1977 | Kamada et al. | 210/500.43 |
| 4,056,467 | 11/1977 | Christen et al. | 210/638 |
| 4,545,910 | 10/1985 | Marze | 210/500.43 |
| 4,548,769 | 10/1985 | Shimomura et al. | 210/500.43 |
| 5,071,973 | 12/1991 | Keller et al. | 424/486 |

FOREIGN PATENT DOCUMENTS 1327990 8/1973 United Kingdom .

OTHER PUBLICATIONS

Miyama et al., Journal of Applied Polymer Science, vol. 35, pp. 115-125 (1988).

*Primary Examiner*—Robert A. Dawson
*Assistant Examiner*—Sun Uk Kim
*Attorney, Agent, or Firm*—Bell, Seltzer, Park & Gibson

[57] ABSTRACT

A composite material is disclosed that comprises a support membrane coated with an additive that reduces the thrombogenic character of the support. The support membrane is a copolymer of acrylonitrile and at least one ionic or ionizable monomer. The additive is a copolymer of acrylonitrile in which at least one of the comonomers is polyoxyethylene. The composite material of the invention is useful in the treatment of blood, and in particular, dialysis and plasmapheresis.

9 Claims, 5 Drawing Sheets

HAEMOCOMPATIBLE COMPOSITE MATERIAL AND METHOD OF USING THEREOF

FIELD OF THE INVENTION

The present invention relates to composite materials useful in the extracorporeal treatment of blood. More specifically, the materials of the present invention may be used in dialysis and plasmapheresis. The materials comprise a support membrane adsorptively coated with an additive that reduces the thrombogenic character of the support.

BACKGROUND

Blood circulates through vessels of the human body and these vessels have a surface adapted for this purpose, i.e., a nonthrombogenic surface. Platelets do not adhere to such nonthrombogenic surfaces and so there is no coagulation.

Extracorporeal circulation of blood for treatment purposes necessitates contact between the blood and an artificial surface. Thus, in dialysis the blood comes into contact with various hoses and the dialysis membrane. The same applies to plasmapheresis, or exposure of the blood to immobilized enzymes or other substances intended for purification.

When blood contacts an artificial surface, the coagulation system is activated, depositing blood platelets, leading to thromboses, which occur either locally in contact with the artificial surface, or more generally within the human body.

The materials used for the extracorporeal circulation and treatment of blood are selected for biocompatibility, and especially haemocompatibility. However, this is not always sufficient. Therefore, workers have attempted to improve such materials by means of various treatments.

Thus, Miyama describes a material formed by graft copolymerization of methoxypolyethylene glycol methacrylate and polyacrylonitrile thioamide. Miyama et al., *Journal of Applied Polymer Science*, "Graft Copolymerization of Methoxypoly(ethylene glycol) Methacrylate Onto Polyacrylonitrile and Evaluation of Nonthrombogenicity of the Copolymer", 35, 115-125 (1988). The authors disclosed an improvement in the nonthrombogenic character of the graft copolymer compared to the acrylonitrile polymer.

However, obtaining such a copolymer necessitates the use of a particular production process. Indeed, the techniques described by Miyama do not make it possible to improve, using relatively simple operations, the nonthrombogenic character of a support membrane without substantially modifying its nature.

It is advantageous to be able to preserve the nature, as well as the properties, of certain existing support membranes while at the same time improving their haemocompatibility.

SUMMARY OF THE INVENTION

To this end, the present invention provides a composite material comprising a support membrane formed from a copolymer of acrylonitrile and at least one ionic or ionizable monomer, on which membrane is adsorbed an additive that reduces the thrombogenic character of the support. The additive is a copolymer in which at least one of the monomers is the polyoxyethylene unit with a degree of polymerization greater than or equal to three, and in which acrylonitrile is a comonomer.

The adsorption of the additive makes it possible to preserve the chemical nature of the support membrane and, therefore, its properties. The improvement in the adsorption of the additive on the support membrane is achieved by virtue of the interactions existing between the acrylonitrile groups of the additive and those of the support.

Thus, by virtue of a simple treatment process, it is possible to improve markedly the nonthrombogenic character of a support.

By adsorption is meant physical bonds such as ionic bonds, Van der Waals bonds, and hydrophilic and hydrophobic bonds.

Coating by adsorption is economical compared to other treatments such as bulk grafting. Indeed, maximum efficacy is achieved for a minimum quantity of additive used, since a superficial layer of additive is sufficient to obtain the desired effect.

According to a particularly advantageous embodiment of the invention, the degree of polymerization of the polyoxyethylene is equal to 23.

Thus, the polyoxyethylene chains are sufficiently long to cause, at the surface of the membrane, a certain steric hindrance which prevents the deposition of platelets and fibrinogen. In addition, the hydrophilic character of the polyoxyethylene leads to the formation of an aqueous environment at the surface of the support that contributes to the biocompatible character of the membrane.

According to a particular embodiment of the present invention, the additive additionally comprises a positively charged comonomer.

This positive charge, which can derive from a quaternary ammonium for example, improves the anchoring between the additive and the support by virtue of a ionic bond.

BRIEF DESCRIPTION OF THE DRAWINGS

FIG. II illustrates the reduction in the platelet adhesion by the material of the invention compared to a material of the prior art, in the absence of red blood cells.

FIG. III illustrates the reduction in the platelet adhesion induced by the material according to the invention compared to a material of the prior art, in the presence of red blood cells.

FIGS. IV, V and VI illustrate the assay results of the plasma levels of fibrinopeptide A, Beta-thromboglobulin, and activated protein C3a, respectively, in X-vivo dialysis tests using materials of the present invention as compared to material of the prior art.

DETAILED DESCRIPTION

The support membranes according to the present invention consist of a copolymer of acrylonitrile and at least one ionic or ionizable monomer, such as those described in the publishied patent specification GB 1,327,990. The ionic or ionizable monomers are essentiaily monomers that are olefinically unsaturated and comprise at least one functional group such as the sulphonic acid group or phosphonic acid group. The acid groups are preferably in the form of salts, such as the sodium, potassium or ammonium salts.

A preferred example of a support membrane is a membrane of acrylonitrile and sodium methallylsulphonate, such as the dialysis membrane HOSPAL AN 69 ®. A plasmapheresis membrane consisting of methyl methacrylate and acrylonitrile is another example of a preferred membrane.

The additive of the present invention is a copolymer wherein one of the comonomers is acrylonitrile and at least one of the comonomers is a polyoxyethylene macromonomer $(CH_2CH_2O)_n$. The degree of polymerization (n) of the polyoxyethylene macromonomer (macromer) is variable, but greater than or equal to three. In fact, the greater the degree of polymerization, the greater the length of the chains and, therefore, the more the aqueous environment, which is created by the hydrophilicity of the polyoxyethylene, will represent a thin layer. This environment is extremely haemocompatible. In addition, the polyoxyethylene chains cause a steric hindrance at the surface of the support, which prevents the deposition of platelets and the adsorption of fibrinogen.

It has been suggested that these flexible chains act as cilia, whose movement prevents the deposition of platelets or fibrinogen.

Among the polyoxyethylene macromonomers suited to the present invention, particular mention is made of triethylene glycol polyacrylate, nonaethylene glycol methacrylate, methoxynonaethylene glycol methacrylate and methoxy-23-ethylene glycol methacrylate.

In order to improve the anchoring of the additive to the support, at least one positively charged monomer is added to the additive. In the case of a support having electronegative sites, such as the sulphonate sites of the membrane HOSPAL AN 69 (a registered trademark of Hospal Industrie), this positive charge will permit the creation of ionic bonds strengthening the adsorption of the additive to the support. The positive charge can be that of a quaternary ammonium, e.g., trimethylaminoethyl methacrylate chloride.

The adsorption of the additive on the support membrane can be effected by slowly circulating the additive, in contact with the support membrane, in a buffer solution at the suitable pH, then by rinsing the support copiously with this buffer solution.

In the case where the support membrane is in the form of hollow fibers arranged inside a haemodialyser, the adsorption can be effected by slow injection of the additive into a Tyrode buffer (NaCl, KCl, NaHCO$_3$, NaH$_2$PO$_4$—H$_2$O) for example.

The qualities exhibited by the composite material according to the present invention, i.e., reducing the adsorption of fibrinogen and the adhesion of platelets, can be tested by measuring radioactivity after labelling the fibrinogen and the platelets, for example with iodine-125 and indium-111, respectively.

EXAMPLE 1

An additive suitable for the present invention is produced by radical copolymerization of acrylonitrile and methoxypolyethylene glycol monomethacrylate. A(n) designates the polyethylene glycol methacrylate, whose degree of polymerization is n, and B designates the acrylonitrile.

Dimethylformamide (DMF), dimethyl sulphoxide (DMSO) and the acrylonitrile (B) are distilled twice over CaH$_2$, at reduced pressure. The azobisisobutyronitrile used as initiator is crystallized from a methanol toluene solution.

The methoxypolyethylene glycol methacrylates A(5), A(8) and A(21) are used directly as provided by Polysciences.

The monomers, the solvent, and the initiator are introduced into a double-walled glass reaction vessel equipped with a magnetic or mechanical stirrer and connected to an external thermostat allowing the temperature to be controlled to ±0.1° C.

The system is then degassed by means of 3 successive cycles of evacuating and flushing with argon, and the reaction is then carried out at a constant temperature of 60° C. under a slight argon pressure.

The consumption of acrylonitrile is monitored by gas-liquid chromatography.

The recovery and purification of the copolymers are effected using one of the following procedures, depending on the composition of the sample:

a) the copolymers low in polyoxyethylene methacrylate are precipitated from the reaction medium in distilled water in excess (10-fold), and they are then purified by precipitation in water from their solution in DMF, followed by rough washing with methanol in a mixer; or b) the copolymers rich in polyoxyethylene methacrylate are precipitated from the reaction medium in diethyl ether in excess (ten-fold); they are then dissolved in distilled water, and the solutions are then completely dialyzed for at least 48 hours, using Spectrapor cellulose membranes whose cut-off threshold is 3,000 daltons.

The copolymers are then lyophilized if it is desired to preserve them.

EXAMPLE 2

An additive suitable for the present invention is produced by copolymerization of the following reaction mixture:

commercial trimethylaminoethyl methacrylate chloride, acrylonitrile, methoxypolyethylene glycol methacrylate whose degree of polymerization is 23. The copolymerization is carried out at 30° C., in the presence of KClO$_3$ and NaHSO$_3$ in aqueous medium.

The table below shows, for two samples X and Y, the molar composition in monomers in the initial reaction mixture (f) and in the copolymer obtained (F), as well as the corresponding mass composition (W) in the copolymer.

TABLE 1

| SAMPLE | | A | B | C |
|---|---|---|---|---|
| X | f | 0.025 | 0.028 | 0.947 |
| Not soluble | F | 0.019 | 0.187 | 0.794 |
| in water | W | 0.015 | 0.810 | 0.165 |
| Y | f | 0.033 | 0.050 | 0.917 |
| Soluble | F | 0.026 | 0.228 | 0.746 |
| in water | W | 0.018 | 0.840 | 0.132 |

Monomer A: Trimethylaminoethyl methacrylate chloride
Monomer B: Polyethylene glycol macromer (MG 23)
Monomer C: Acrylonitrile

EXAMPLE 3

Fibers consisting of a copolymer of acrylonitrile and sodium methallylsulphonate are used as the support membrane: HOSPAL AN 69 TM.

These fibers, which are 48 in number, are inserted in a haemodialysis mini-module. The internal diameter of the fibers is 270 μm and their length is approximately 20 cm.

The additive used is the terpolymer Y obtained in Example 2. This terpolymer Y is in solution in ST (Simple Tyrode) buffer whose composition 1 liter is as follows:

NaCl: 8 g
KCl: 0.2 g
NaHCO$_3$ : 1 g
NaH$_2$PO$_4$-H$_2$O: 0.06 g

In order to obtain the composite material of the present invention, the internal surface of the hollow fibers is treated by adsorption, by slowly injecting inside the mini-module a solution of terpolymer Y in the ST buffer, and by then rinsing copiously with this buffer, whose pH is 7.5.

The parameters of this adsorption are the following:
concentration of the terpolymer in solution: 5 g/l
volume of solution injected: 25 ml
rate of injection: 0.1 ml/min
ambient temperature

EXAMPLE 4

The adsorption of fibrinogen is tested on a mini-module obtained in accordance with Example 3.

To this end, a solution of fibrinogen is labelled with iodine-125 in accordance with the Iodo-gen technique.

Figure 1:
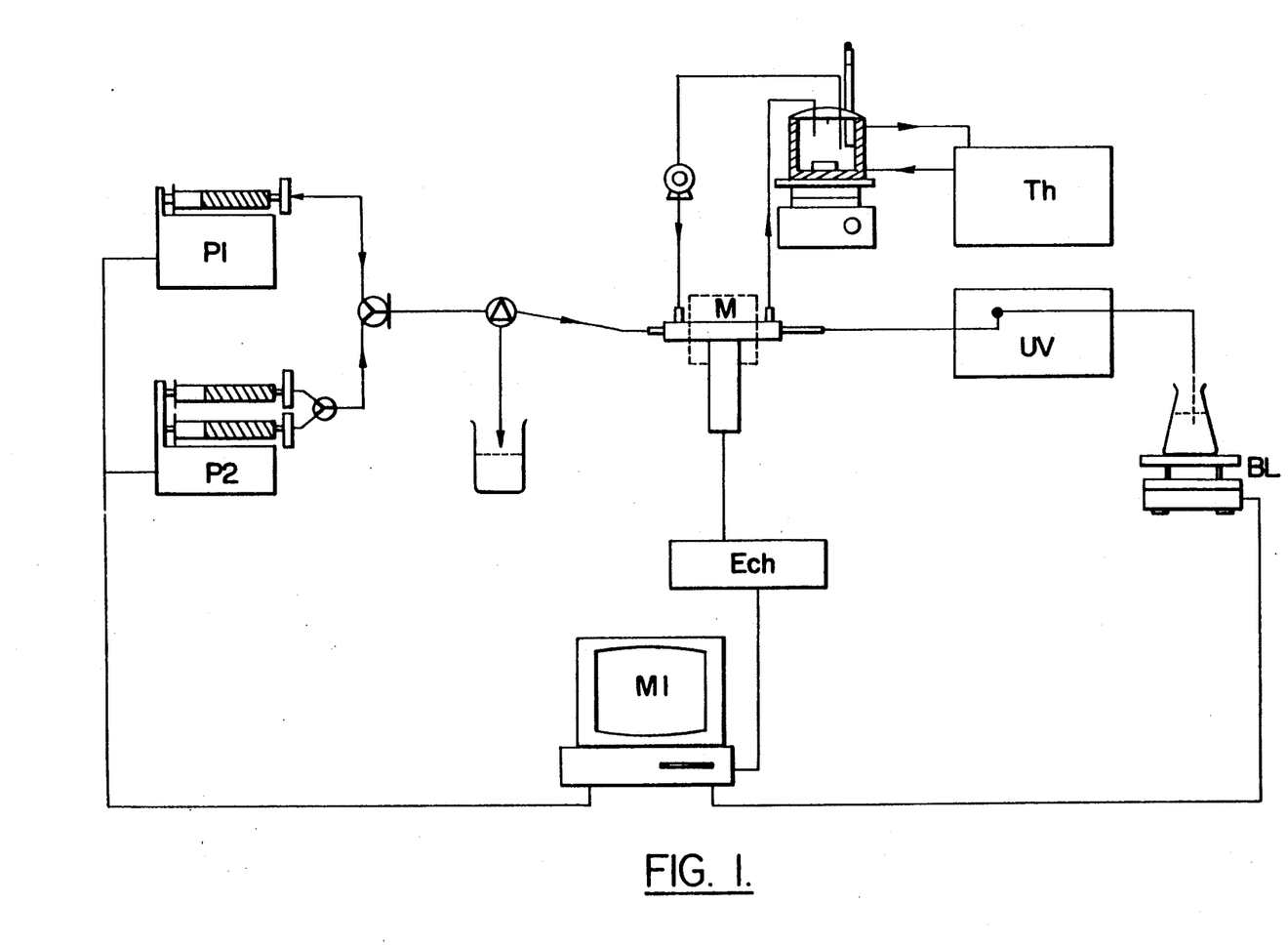
FIG. 1 shows, diagrammatically and with no specific scale, an experimental set-up which makes it possible to demonstrate the improvement in the nonthrombogenetic properties of the material according to the invention.
Figure 2:
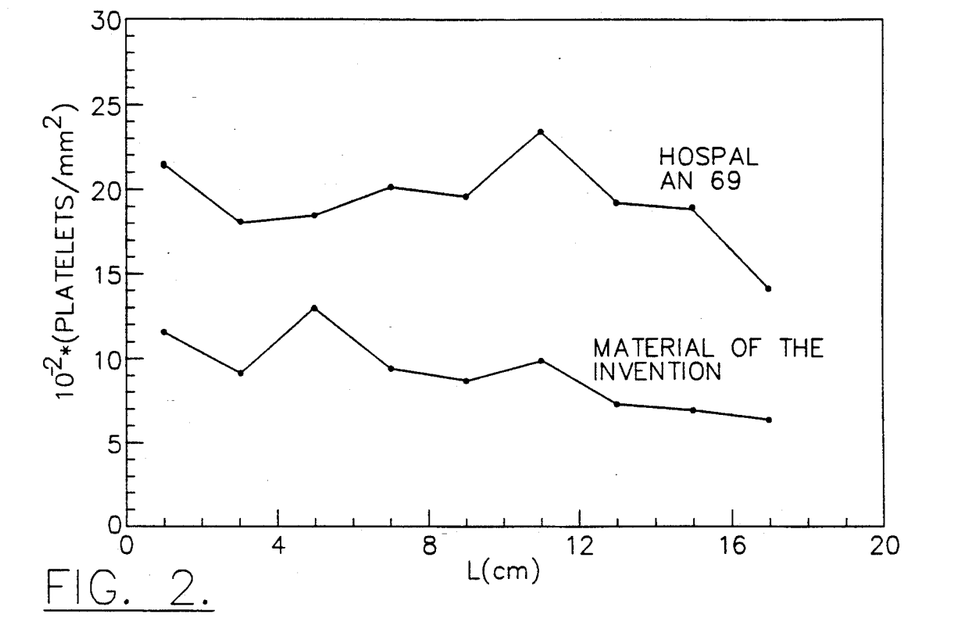
Figure 3:
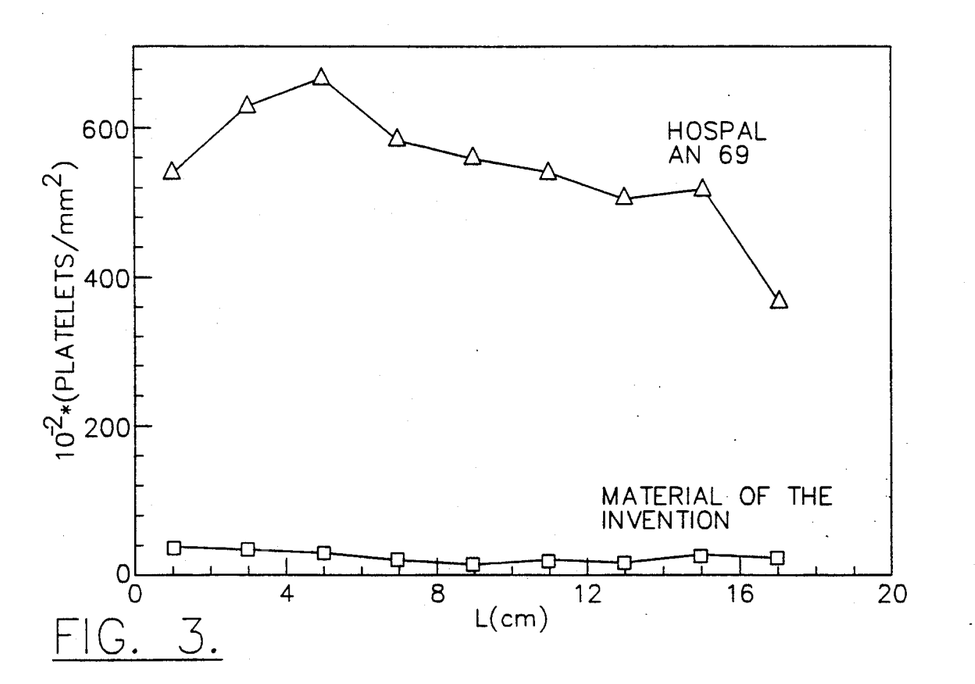
Figure 4:
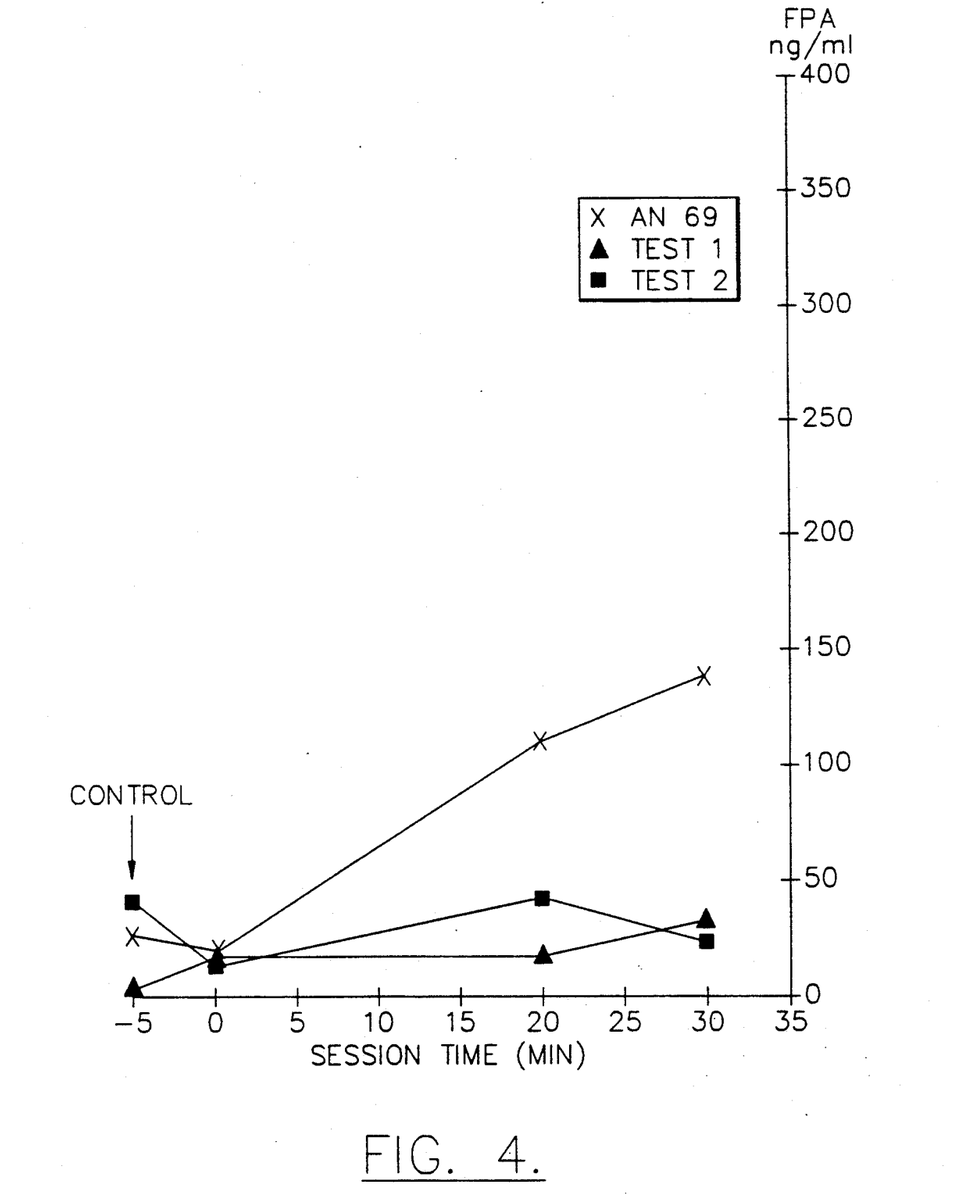
Figure 5:
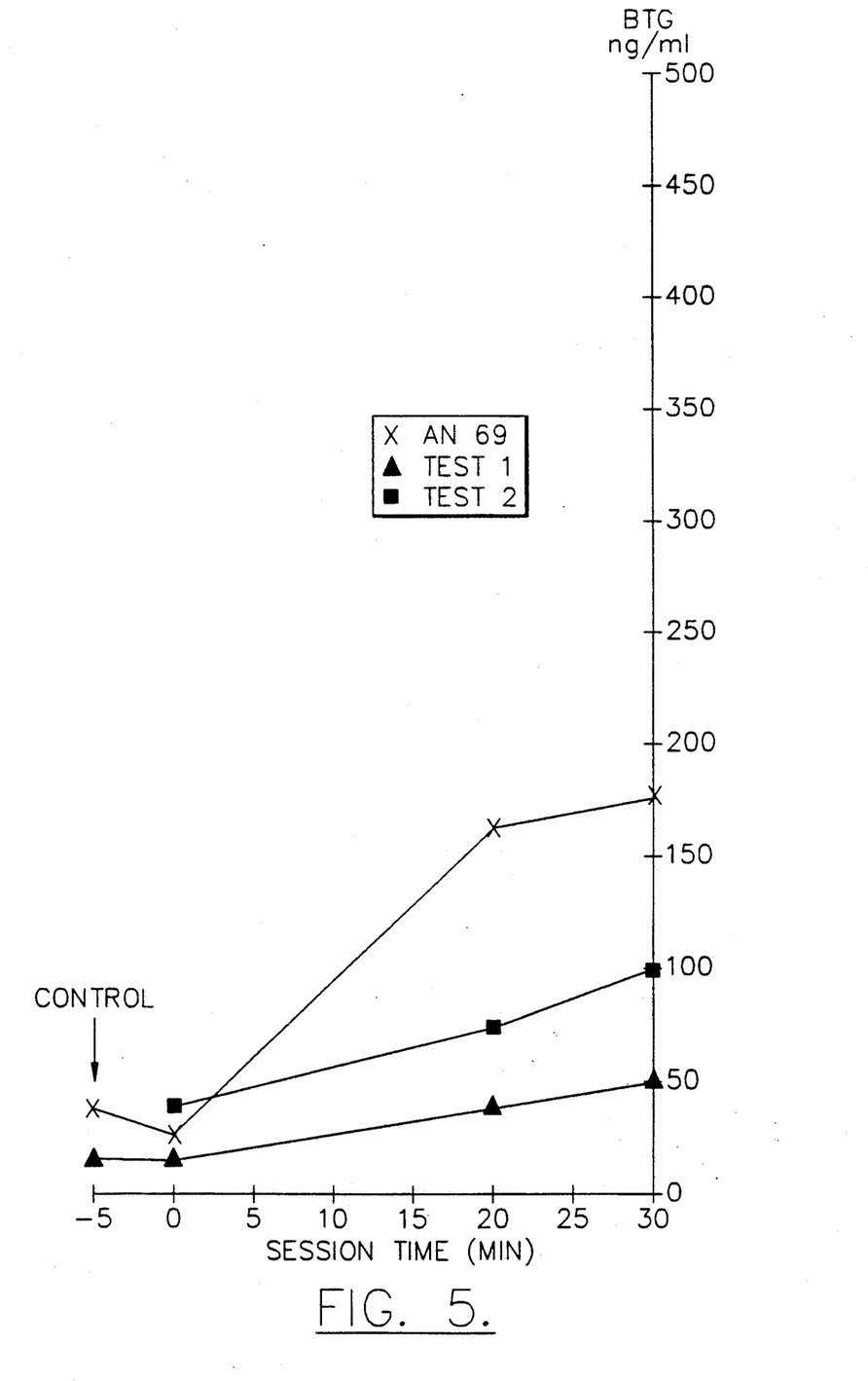
Figure 6:
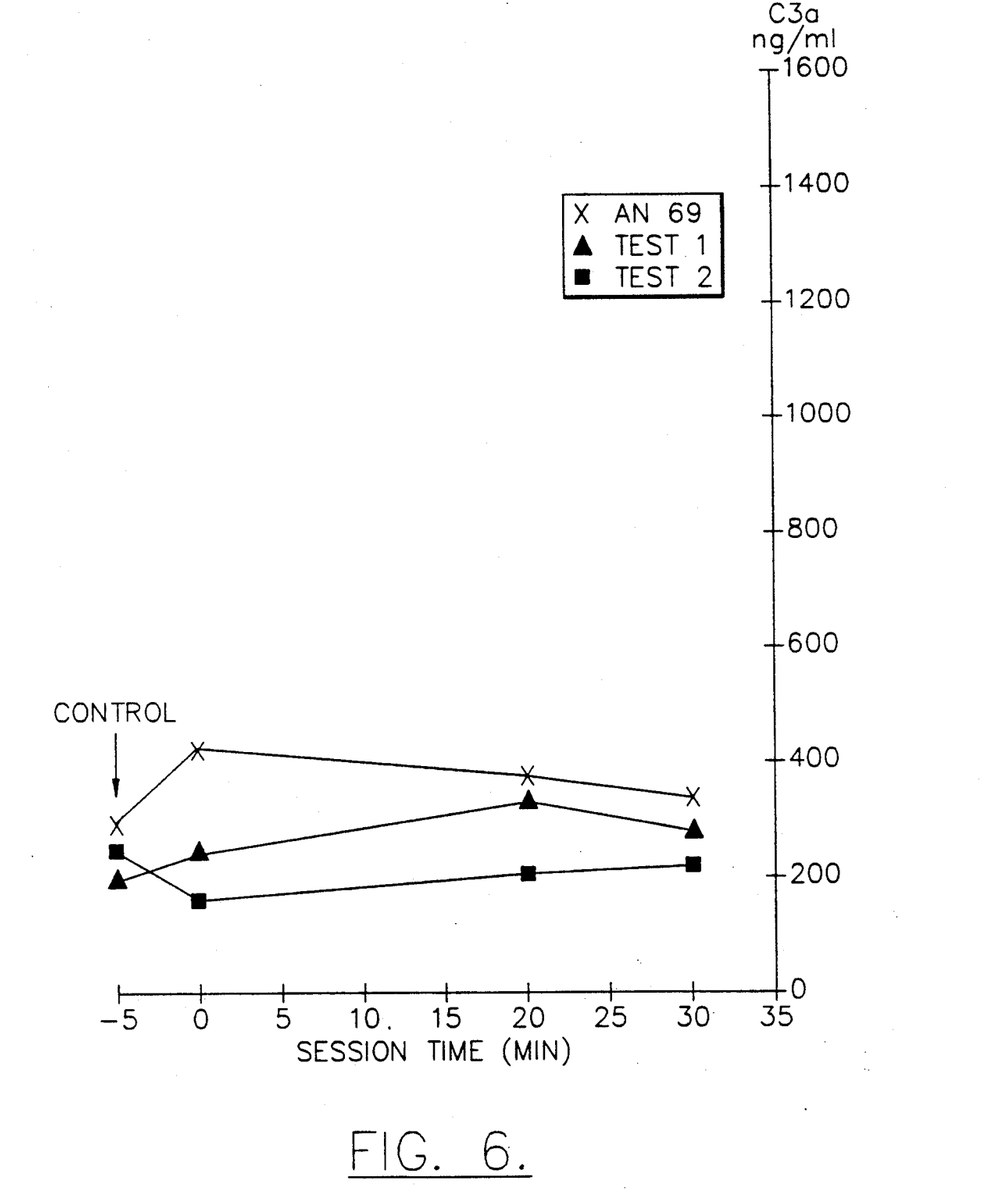

The fibrinogen adsorption kinetics are effected using the experimental set-up described below:

Two syringe pushers P1 and P2, one containing the solution and the other containing the solvent, are controlled by a microcomputer M1. The total output, the concentration of the injected solution, the duration and the number of passages of the solution can thus be programmed. Connected via a Teflon tube to the two syringe pushers, the mini-module M is placed in a slot in a detector (NaI crystal), which is connected to a counting scale Ech, which is also linked to the microcomputer M1. On leaving the module M, the solution is first directed towards a UV cell for checking the protein concentration; it is then collected in a vessel positioned on electronic scales BL, of which the data is acquired by the microcomputer M1. All the instantaneous kinetic data are displayed on the screen and recorded in a register, which can be used for a subsequent treatment.

The thermostating of the mini-module at 37° C. is effected by circulating the buffer in the dialysate compartment. The flow rate of this buffer is controlled by a flowmeter.

The fibrinogen solution is introduced into the mini-modules by means of the displacement of the buffer, in order to prevent the formation of an air-solution interface. The passage of the radioactive suspension or solution is framed by two passages of buffer of the same duration.

The duration of the passage of the solution and the duration of each rinsing by means of the buffer are equal to 25 min. The flow rate is fixed at 2 ml/min.

Following experiment, the fiber bundles are cut into 2-cm pieces in order to determine the surface concentration as a function of the position on the bundle.

In order to show the efficacy of the additive as regards to the reduction in the adsorption of the fibrinogen, the same experiment is carried out on a mini-module of hollow fibers consisting of the composite material according to the present invention (obtained in accordance with Example 3) and a mini-module of hollow fibers consisting of the HOSPAL AN 69 TM membrane.

The table below collates the results obtained for 3 series of comparative tests, carried out using solutions of different fibrinogen concentrations.

TABLE 2

| Module | Fibrinogen concentration (g/l) | $\gamma$ ($S^{-1}$) | Slope (CPM/s) | k ($10^{-5}$ cm/s) | $\Gamma$ (g/cm$^2$) | R |
|---|---|---|---|---|---|---|
| A | 0.0055 | 370 | 159.5 | 101.5 | 0.67 | 0 |
| A treated | 0.0063 | 370 | 17.3 | 11.0 | 0.085 | 88.0 |
| B | 0.0050 | 518 | 139 | 105.5 | 0.73 | 0 |
| B treated | 0.0047 | 522 | 7.36 | 4.0 | 0.019 | 97.0 |
| C | 0.339 | 505 | 563 | 9.89 | 4.86 | 0 |
| C10 treated | 0.316 | 505 | 133 | 3.07 | 0.618 | 87.3 |

$\gamma$ expresses the rate of shearing.
$\Gamma$ represents the superficial interface concentration of fibrinogen at a time t.
k is the apparent adsorption constant of the fibrinogen, which permits comparison of the results, without the fibrinogen concentration of the solution.
The slope, expressed in CPM/s (counts per minute per second) is representative of the kinetics of the adsorption phenomenon.

In these three series of tests it is observed that the mini-modules containing a material according to the invention adsorb for less fibrinogen than do the controls, the reduction varying between 87 and 97%.

EXAMPLE 5

The kinetics of platelet adhesion are studied comparatively, using a mini-module of hollow fibers consisting of composite material according to the present invention, and with a mini-module of hollow fibers of HOSPAL AN 69 TM membrane serving as a control The experimental set-up is that of the preceding example.

The platelets are labelled with indium-111 in TA buffer (Tyrode Albumin 0.35%). The duration for the passage of the platelet suspension is variable (5 or 10 minutes); in contrast, the time for each rinsing is fixed at 3 minutes.

Our results show an nonthrombogenic character of the material according to the invention compared to the control-membrane Our results were plotted as the surface platelet concentration as a function of the distance with respect to the entry of the mini-module. The platelet concentration of the solution used is 300,000 pl/μl, the duration of contact between the surface of the fibers and the platelet solution is 10 minutes; the rate of shearing is 500 $S^{-1}$, and the reaction is carried out at 37° C. The platelet solution contains no red blood cells.

In the absence of red blood cells, the platelet adhesion is low, but the composite material according to the invention produces a platelet adhesion which is 40 to 50% lower than the platelet adhesion observed on the control fibers.

EXAMPLE 6

The experimental conditions are the same as those in the preceding example.

The platelets are dissolved in a solution containing 40% of red blood cells, which correspond fairly well to the concentration of the blood in the case of the normal haematocrit. The platelet concentration is thus 180,000 pl/μl.

The rate of shearing is 500 $S^{-1}$ and the reaction is carried out at ambient temperature.

Our results were charted for each of the mini-modules (according to the invention and according to the control module), by plotting activity as a function of time.

Under the conditions, once again the platelet adhesion is distinctly less when using the composite material according to the invention than when using the control hollow fibers.

EXAMPLE 7

The biocompatibility of the material of the subject invention is evaluated by measuring the levels of fibrinopeptide A,β thromboglobulin and C3 a protein during ex-vivo dialysis sessions.

To this end, use is made of mini-dialysers with hollow fibers whose characteristics are as follows;
HOSPAL AN 69 TM membrane;
internal diameter of fibers: 240 μm;
external diameter of fibers: 340 μm;
number of fibers: 340;
inner surface: 512 $cm^2$;

After rinsing the mini-dialysers with an aqueous solution of NaCl at 0.9 g/l, two of them are treated by adsorption of the additive Y obtained in accordance with Example 2. A third one is conserved intact to serve as a control. The treatment by adsorption is carried out by passing through the fibers a polymer solution at 5 g/l in a simple tyrode buffer.

5 ml are passed at a rate of 6 ml/min, then 17 ml at a rate of 0.1 ml/min.

After treatment, the dialysers are rinsed using an aqueous solution of NaCl at 0.9 g/l, heparinized at 2.5 IU/ml for the blood compartment.

To carry out the ex-vivo tests, the rinsing liquid is retained in the dialysate compartment by closing the intake and outlet points of the dialysis fluid, and the blood of a donor is passed into the blood compartment at a rate of 10 ml/min for 34 min. The rate of shearing is 360 $S^{-1}$. After its passage through the haemodialyser, the blood is not returned to the patient.

The assay of a certain number of plasmatic substances is then carried out, which makes it possible to evaluate the biocompatability of the material.

We determined the plasma level of fibrinopeptide A in two tests carried out with the material of the invention, as well as the control consisting of a HOSPAL AN 69 TM membrane without additive.

Fibrinopeptide A is an early indicator of activation of the phenomenon of coagulation.

Our results show a clear improvement in the non-thrombogenic character of the material of the present invention.

We also determined the plasma levels of β-thromboglobulin, which is an indicator of the platelet activation.

Here again, we observed the highly satisfactory performance of the material of the present invention compared to the prior art.

We also performed a plasma assay of activated protein C3a, the presence of which indicates activation of the complement system.

The results obtained with the material of the invention are substantially equal to those obtained with the HOSPAL AN 69 TM membrane which is already renowned for its performance in this regard. Thus, the high quality of the support is maintained upon adsorption of the additive Y.

EXAMPLE 8

The sustaining of the performance (dialysis and permeability) of the material of the invention compared to the support not covered with the additive is verified.

To this end, use is made of a mini-dialyzer equipped with 170 fibers of HOSPAL AN 69 ® membrane.

The following measurements are effected on this dialyzer:
Ultrafiltration
Urea clearance
Vitamin $B_{12}$ clearance.

After carrying out these measurements, the dialyzer is treated by adsorption of the terpolymer Y in the same way as in the preceding example. A material according to the present invention is thus obtained.

The ultrafiltration is once again measured, as are the urea clearance and vitamin $B_{12}$ clearance.

The measurements carried out are corrected to bring them to the same flow rate conditions at the inlet of the blood compartment (namely 3.5 ml/min) and of the dialysate compartment (namely 10.5 ml/min), the ultrafiltration flow rate being zero.

The results before and after treatment are collected in the table below:

TABLE 3

| Clearance | Ultrafiltration in ml/H · $m^2$ · mmHg | Urea Clearance | Vit $B_{12}$ |
|---|---|---|---|
| Before treatment | 52 | 3.1 | 1.5 |
| After treatment = invention | 48 | 3.1 | 1.5 |

The results show that the performance of the material are sustained when it is covered by adsorption with the additive Y. (The apparent fall as regards ultrafiltration is no doubt due to the conditions of the measurement, which it was only possible to carry out after 2 days).

We claim:

1. A composite material comprising a support membrane formed from a copolymer of acrylonitrile and at least one ionic or ionizable monomer, on which membrane is adsorbed an additive that reduces the thrombogenic character of the support, said additive comprising:
    a copolymer in which at least one of the monomers comprises a polyoxyethylene unit with a degree of polymerization of at least three; and in which acrylonitrile is a comonomer.

2. The material of claim 1, wherein one of the comonomers of the additive comprising the polyoxyethylene unit is methoxypolyethylene glycol methacrylate.

3. The material of claim 1, wherein the degree of polymerization of the polyoxyethylene is 23.

4. A composite material comprising a support membrane formed from a copolymer of acrylonitrile and at least one ionic or ionizable monomer, on which membrane is adsorbed an additive that reduces the thrombogenic character of the support, said additive comprising a copolymer:
    a) in which at least one of the monomers comprises a polyoxyethylene unit with a degree of polymerization of at least three;

b) in which acrylonitrile is a comonomer; and c) which additionally comprises a positively charged comonomer.

5. The material of claim 4, wherein the positively charged comonomer is a quaternary ammonium.

6. The material of claim 4, wherein the positively charged comonomer is a trimethylaminoethyl methacrylate halide.

7. The material of claim 4, wherein the additive consists essentially of:

a.) 23 mole % of methoxypolyethylene glycol methacrylate;

b.) 74.5 mole % of acrylonitrile; and c.) 2.5 mole % of positively charged comonomer.

8. The material of claim 1 or 4, wherein the support membrane consists essentially of a copolymer of acrylonitrile and sodium methallylsulphonate.

9. A method of blood dialysis which comprises circulating blood into contact with the composite material of claim 1 or 4.

* * * * *